(12) United States Patent
Ben-David et al.

(10) Patent No.: US 10,118,190 B2
(45) Date of Patent: *Nov. 6, 2018

(54) SCENT DISPENSING APPARATUS AND METHOD FOR THE CONTROL THEREOF

(71) Applicants: Yoav Ben-David, Tel Aviv (IL); Moshe Zach, Hod Hasharon (IL)

(72) Inventors: Yoav Ben-David, Tel Aviv (IL); Moshe Zach, Hod Hasharon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/917,689

(22) Filed: Mar. 11, 2018

(65) Prior Publication Data

US 2018/0193861 A1    Jul. 12, 2018

Related U.S. Application Data

(63) Continuation of application No. 15/500,574, filed as application No. PCT/IL2016/050093 on Jan. 28, 2016, now Pat. No. 9,943,870.

(60) Provisional application No. 62/111,754, filed on Feb. 4, 2015.

(51) Int. Cl.

| B05B 17/04 | (2006.01) |
|---|---|
| B05B 12/02 | (2006.01) |
| H04L 29/00 | (2006.01) |
| H04L 29/08 | (2006.01) |
| B05B 17/06 | (2006.01) |
| A61L 9/12 | (2006.01) |
| B60R 16/08 | (2006.01) |

(52) U.S. Cl.
CPC ............... *B05B 12/02* (2013.01); *A61L 9/12* (2013.01); *B05B 17/0607* (2013.01); *B05B 17/0669* (2013.01); *H04L 29/00* (2013.01); *H04L 29/08* (2013.01); *H04L 67/04* (2013.01); *H04L 67/1061* (2013.01); *H04L 67/12* (2013.01); *H04L 67/125* (2013.01); *B60R 16/08* (2013.01)

(58) Field of Classification Search
CPC . B05B 12/02; B05B 17/0607; B05B 17/0669; H04L 67/1061; H04L 67/125
USPC .... 239/4, 102.1, 102.2, 67, 69, 71; 700/282, 700/283; 422/124
See application file for complete search history.

(56) References Cited

U.S. PATENT DOCUMENTS

| 6,802,460 B2 * | 10/2004 | Hess et al. | A61L 2/22 239/102.2 |
|---|---|---|---|
| 9,943,870 B2 * | 4/2018 | Ben-David et al. | B05B 12/02 239/1 |
| 2008/0061163 A1 * | 3/2008 | Kubby et al. | A01M 1/205 239/102.1 |

* cited by examiner

*Primary Examiner* — Steven J Ganey
(74) *Attorney, Agent, or Firm* — The Law Office of Joseph L. Felber

(57) ABSTRACT

An apparatus for dispensing compounds bearing scent in which one or more scent dispensing units contain each one scent bearing compound and is activated mechanically by an electromechanical activator. A user handled device contains a controller, a memory and a communications device. Resident hardware includes a resident channel for communicating with the user handled device and a controlled driver for controlling the scent dispenser mechanically. A wireless peer to peer communications system carries out the communications between the user device and the resident hardware. The user can input parameter for controlling the dispensing unit through a user device interface. A controller in the resident hardware implements a dispenser activation scheme, mechanically expressed by the activator of the scent dispensing unit.

14 Claims, 6 Drawing Sheets

SCENT DISPENSING APPARATUS AND METHOD FOR THE CONTROL THEREOF

CROSS-REFERENCE TO RELATED APPLICATIONS

The present application claims the benefit of priority to U.S. Provisional Patent Application Ser. No. 62/111,754 filed 4 Feb. 2015, entitled "Fragrance Activation By Wireless Control".

TECHNICAL FIELD

The present invention generally relates to an apparatus for dispensing scent bearing substances and the control of the dispensation in the air.

BACKGROUND ART

Dispensing chemical compounds for providing scent or fragrance are often used in close quarters, rooms or spaces occupied by humans, in which unpleasant odors may linger and affect the scene if no measures are taken to counter their presence. Special attention is made to cars in which conditions tend to promote the development of unpleasant smell unless treatment is provided. The actual dispensation of the scent compounds can be achieved by spraying, manual or controlled, and also by passive diffusion from open receptacles. In active dispensation, the scent bearing compounds are to be atomized and ejected to the ambient atmosphere. The atomization and ejection are typically powered by ultrasonic energy implementable by piezoelectric actuators, and the droplets produced by the atomization process are ejected through a porous membrane that can allow through droplets of certain size and below. Other nuances of the atomizing scent dispensing system are available. In addition, non atomizing scent dispensing systems are available, for example the system described in U.S. Pat. No. 7,377,493 employs a vacuum inducing mechanism (such as a Venturi tube) to disperse molecules from a liquid surface of a container to the ambient air, spraying in such a case being driven by a high pressure air stream.

DISCLOSURE OF THE INVENTION

Figure 1:
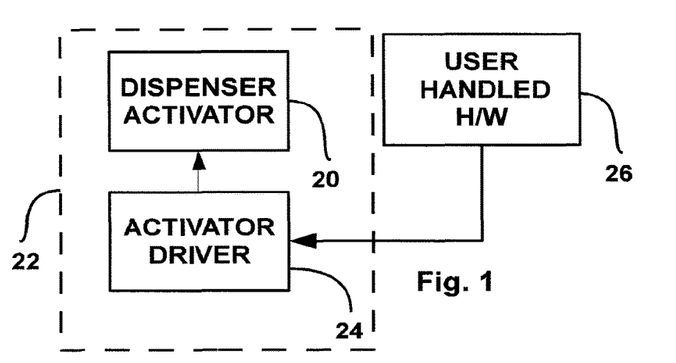
FIG. 1 is a block diagram illustrating a basic scheme of the environment in which the present invention is implemented.

In accordance with the present invention, compounds bearing scent or fragrance are provided to the ambient air controllably. A control system transmits commands wirelessly to a mechanically activated dispensing system that complies with the commands received. As can be seen in FIG. 1 dispenser activator 20 which is part of a scent dispensing unit (SDU) 22, is driven by driver 24 which may or may not constitute a part of SDU 22. User handled hardware (UHH) 26 is a hardware module which includes a processor and memory, such as a smartphone, positioned and handled in a location removed from scent dispensing unit (SDU) 22. The number of scent dispensers deployed is not limited. It may well be considered that several dispensers are deployed, each one containing a different scent compound, so that the user may be able to select one or a combination of scents as he or she desires.

Figure 2:
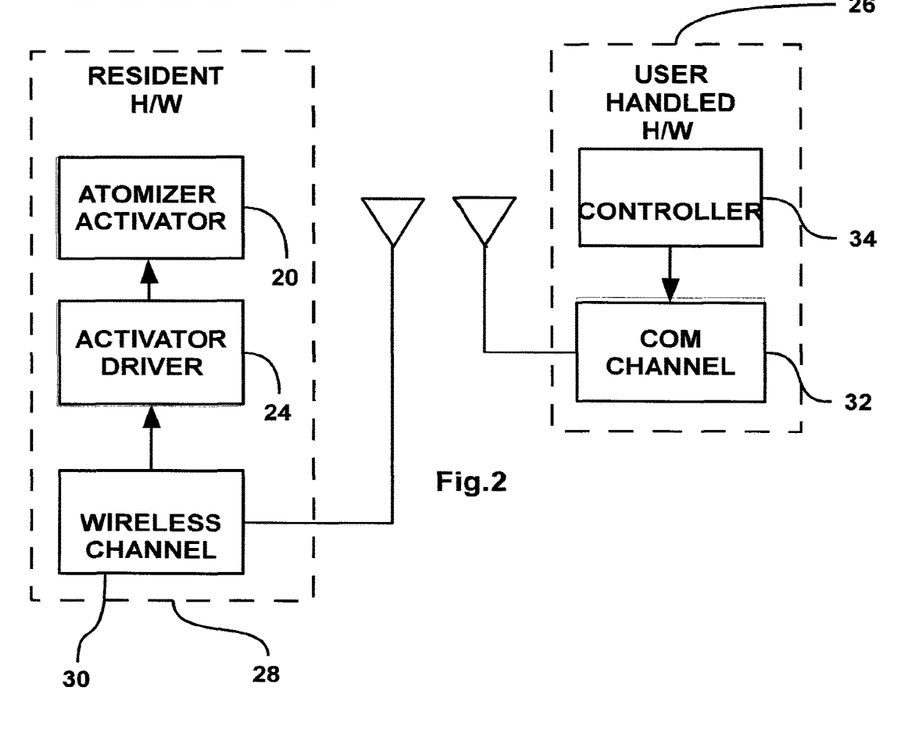
FIG. 2 is a block diagram illustrating a very abstract architecture of a system in accordance with the invention.

In FIG. 2, the aspect of the communications system, central to the present invention is introduced. Resident hardware module 28 includes atomizer activator 20, atomizer activator driver 24 and wireless channel 30. User handled hardware (UHH) 26 includes, among others, a communication channel 32 which intercommunicates with wireless channel 30 of the resident hardware. User handled hardware also includes a controller 34 with the associated memory, and else. Beyond what is described in the drawing, the resident hardware and the user handled hardware can each be described as a separate module whereby a transient wireless connection can be mutually established therebetween.

Figure 3:
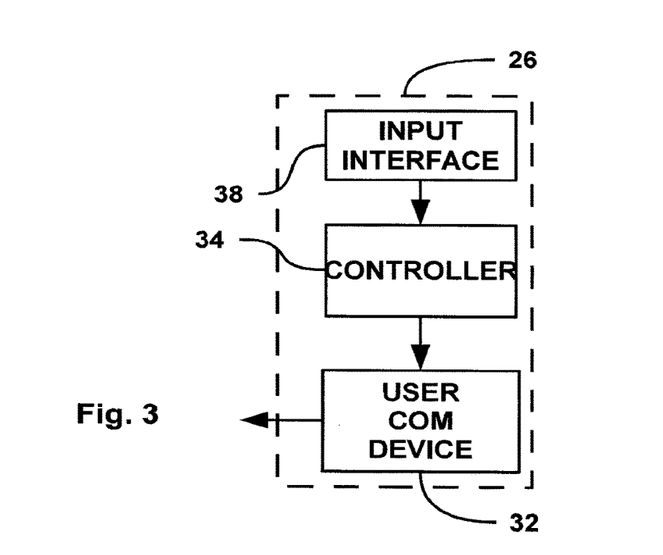
FIG. 3 is a block diagram illustrating as above but with details on the communications aspects.

In FIG. 3, UHH 26, typically a smartphone or a tablet computer with a cellular modem, includes, from the point of view of the present invention, two major parts, exemplified in a car environment: a user communication device 32 which is intercommunicable with the resident wireless channel 30. User input interface 38 represents one or more input devices such as touch screen, keyboard, virtual or real, microphone and speaker through which the user interacts with the system such as introduce instructions to the system. The touch screen also uses as display screen User communications channel 32 of UHH 26, mentioned above optionally and typically supports and substantiates a peer-to-peer network, such as Blue Tooth® (BT) or BLE (stands for BT low energy) which manifests itself commercially in several nuances, and is continuing to develop as a popular short range wireless network for short distances of several meters in range. Noticeable is version 4.0 and above which implements a low energy consumption aspect. In a car situation, whereby a scent dispensing apparatus is placed in the cabin, the native BT of the car, if installed, can be used as the resident communication channel 30. To further explain the architecture of the system of the invention, reference is made to FIG. 4, which illustrates a car scenario in which the native BT system installed in the microenvironment of a car, is made of use in an embodiment of the present invention. Car native BT device 30B implements the car communication device while a personal BT device 32B implements the personal communication device.

In terms of commercially available hardware, the native BT device is optionally a car BT such as a "Bluetooth hands free kit" of any brand available in the market, which incorporates a BT Transceiver. Such a BT transceiver must be compatible with a BT system of a user, such as a wearable BT system or a smartphone containing BT circuitry and an interface. However, a dedicated BT system may be employed in an embodiment of the invention, for the purpose of controlling dispensation of scent materials.

However, the inventor of the present invention does not wish to limit himself the BT, as there are other communication standards available, which may be of lesser convenience but are still practical. It may also be possible to use wired communication means, but this is much less practical in most cases.

Scent Dispenser and Activation Thereof

Figure 5:
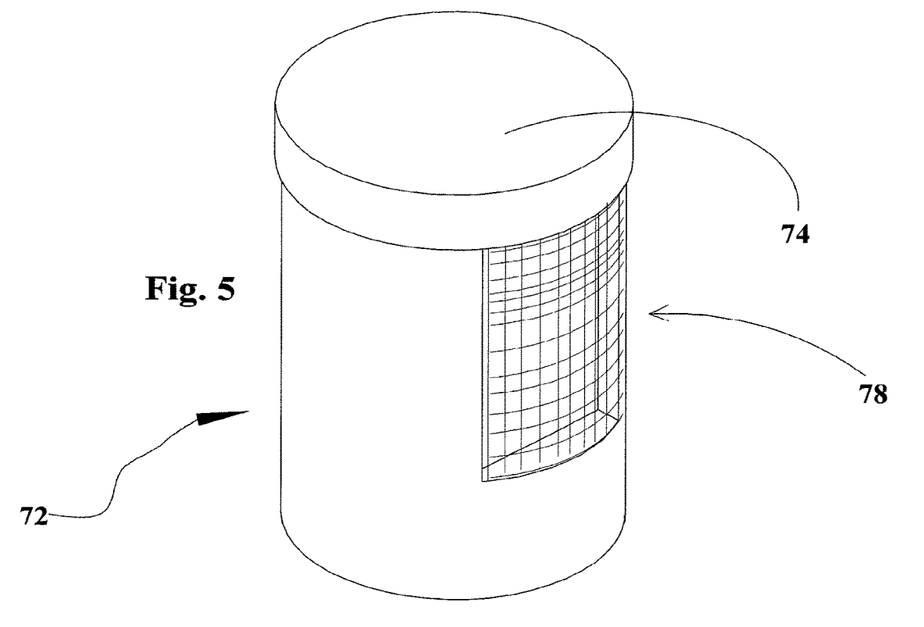
FIG. 5 is an isometric schematic depiction of a scent dispensing unit (SDU) in accordance with the invention.
Figure 6A:
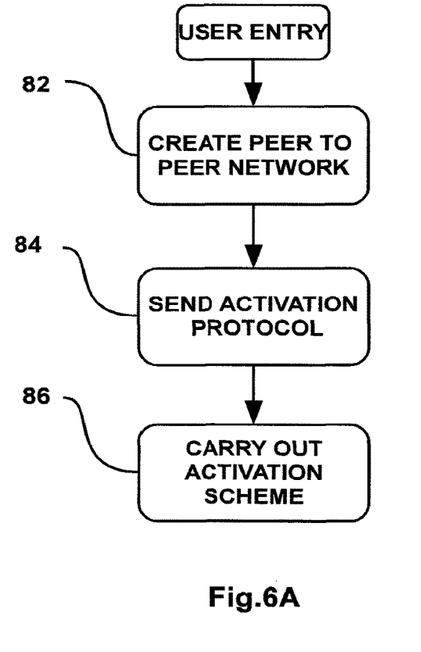
FIG. 6A is a flow chart describing the major sequence of steps carried out in a session of scent dispensation in accordance with the invention.

In accordance with some embodiments of the present invention, the compound/s bearing scent (or fragrance), are distributed to the user in small containers, for example cylindrical in shape. As can be seen in FIG. 5, the scent compound container 72 has an energizing component 74 which includes an electromechanical activator such as a piezoelectric actuator. At the side of container 72, a perforated wall section (also known as a mesh) 78 is disposed, through which droplets of scent bearing compounds can be dispensed to the ambient atmosphere. At times, air bubbles form as a result of the activation forming in the liquid, behind the mesh. Such bubbles can block passage of liquid and in order to prevent such blockage, a wire such as a metal wire or a twisted metal wire can be inserted such that one end is positioned near mesh 78, where the bubbles form, guiding the bubbles along the wire. The bubbles travel along the wire upwards and are prevented from forming a block. The other end of the wire points upwards Dispenser activator 20 is driven by driver 24 (not shown) which receives commands from a controller (not shown). The power for the actuator is obtained from a battery which is installed adjacent container 72. Alternatively, the power is obtained from the electrical system of the vehicle or mains in a room, whichever is pertinent. Yet another energising solution is the one based on photovoltaic sources to charge the battery, the function of which depends of course on the availability of light. The entire structure as described is exemplary, and many forms may be embodied, as long as the action of the energizing attachment is affective as a vibrating component for atomizing the liquid stored inside container 72, and the perforated wall section 78 lets droplets ejection take place. When the activator is quiescent, no much dispensation of scent takes place or none at all, thus saving the contents of container 72. More details about ultrasonic liquid atomizers are available in the public domain. For example published document US 2010/0044460 discloses an ultrasonic liquid atomizer in which a ceramic piezoelectric activator (item 9 in FIG. 4) and a membrane (item 3 in FIG. 4), function together to eject micro-droplets as described in paragraph 0035 there. Atomizer meshes (another name for the membrane) can be purchased at Liga precision Technology co., LTD of No. 17, 21st Road, Taichung Industrial Park, Taichung, Taiwan In FIG. 6A an event flow chart describing the working procedure of scent dispensation and control thereof is carried out in a car. As the user enters the cabin, a peer to peer network is created in step 82, typically automatically, implementing BT communications protocols providing that a connection between the car communication device and the personal device of the user is permitted. The network is made possible once a the step known as "pairing" or "bonding" has been carried out between the user device and the resident device. Forming a network is possible again and again, by which information can flow back and forth between the user system and the car system. Once a wireless network has been formed, the user device is able to send (transmit) an activation protocol to the receiving system in step 84, i.e. to the car communication system. Such a protocol starts the dispensing mechanism and then allows for initiating dispenser activation schemes (DASs), one or more, at step 86. An activation profile (AP) includes activation parameters relating to the frequency parameters of the vibration, frequency of the vibration bursts, number of vibration bursts per unit time (duty cycle), how long each vibration burst lasts, etc. Thus, with each DAS, a specific AP may be associated. The DAS may also be sensitive to physical properties of the near environment such as temperature and humidity, taking in account that the amount of scent bearing compound is increased in high temperatures. In this example, the resonance frequency of the activation mechanism is not measured, or it is measured before activation. The DAS or the AP may include instructions as to the frequency by which the actuator is to function, which typically is to correspond to the resonance frequency of the electromechanical activator. The activation protocol as referred to above (see step 84 in FIG. 6A) is not implemented in all embodiments. The system may be activated as soon as the network is established by implementing an activation protocol stored in the resident hardware, which could be changed later on. The system may also be deactivated as soon as the network is disconnected.

In embodiments of the invention demonstrating increased sophistication and automation, the AP may include response to the mechanical state of the UHH such as measured by sensors mounted in or connected to the UHH. Such inertial hardware or inertial sensors may be connected wirelessly to the UHH or attached to the UHH or to the scent dispenser controller. Such inertial sensors are for example accelerometers, gyroscopes. GPS receivers may be used to obtain data from which movement can be calculated. Additionally, an application that draws information from the cellular system to detect travel motion can also calculate motion. Such information is exploited to determine the activation profile (AP) for improving responsiveness of the SDU to the general state of the. For example, the scent dispensing can be conditioned to be activated only when the car travels.

The activation profile (AP) can also include dependencies on the distance that the UHH and the SDU with its wireless channel as measured by the sensors, in the UHH. The distance traveled can be also measured by the wireless network and or a GPS dependent application.

Figure 6B:
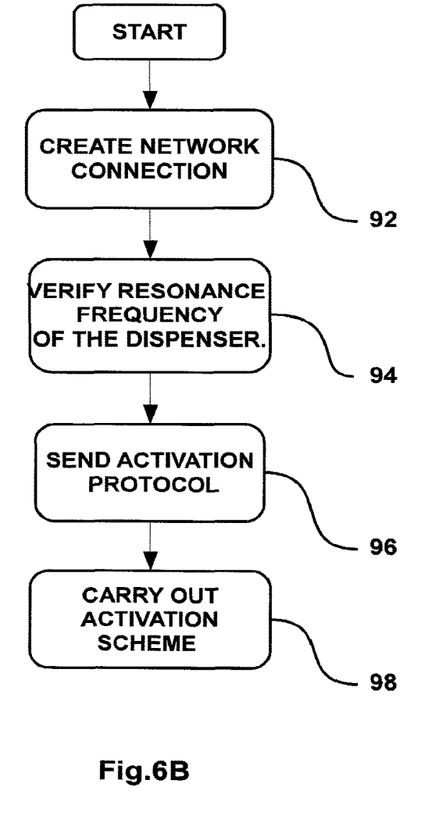
FIG. 6B is a flow chart describing the major sequence of steps carried out in a session of scent dispensation in accordance with the invention, including resonance frequency determination.

In FIG. 6B the working procedure of dispensing scent in accordance with the present invention includes resonance check. At step 92 a peer to peer network is established as described above. At step 94 the resonance frequency of the dispenser is verified. At step 96 activation protocol is sent over to the native device at the car. At step 98 the activation scheme is carried out. In such cases in which the resonance verification is repeated, it is included in the activation scheme.

Frequency Optimization for the Actuator

In order to provide best energetic efficiency for the scent dispensing device (scent dispenser above), it is preferable to vibrate the substance container such as container 72, at its resonant frequency, thereby achieving highest vibration dependent dispersion for a given quantity of power. Since the resonant frequency of the SDU may change in time due to the change in level of liquid, indoors temperature, the resonant frequency is better verified several times between the maximal and minimal levels of liquid in the container 72.

Frequency of actuation is provided for example by a clock circuit or by a controlled PLL (phase locked loop) circuit, which may be located in the user side device and/or at the activator side device. It is also possible to use a UART mechanism (universal asynchronous receiver/transmitter) Such a mechanism can be used to send (transmit) a continuous stream of "55" bytes with no parity bit to provide square wave that by filtering can be converted to sine wave. In this case the frequency can be controlled by selecting and configuring the UART bit rate, which may require hardware implements, associated with the resident activator driver.

Hardware Components

Figure 4:
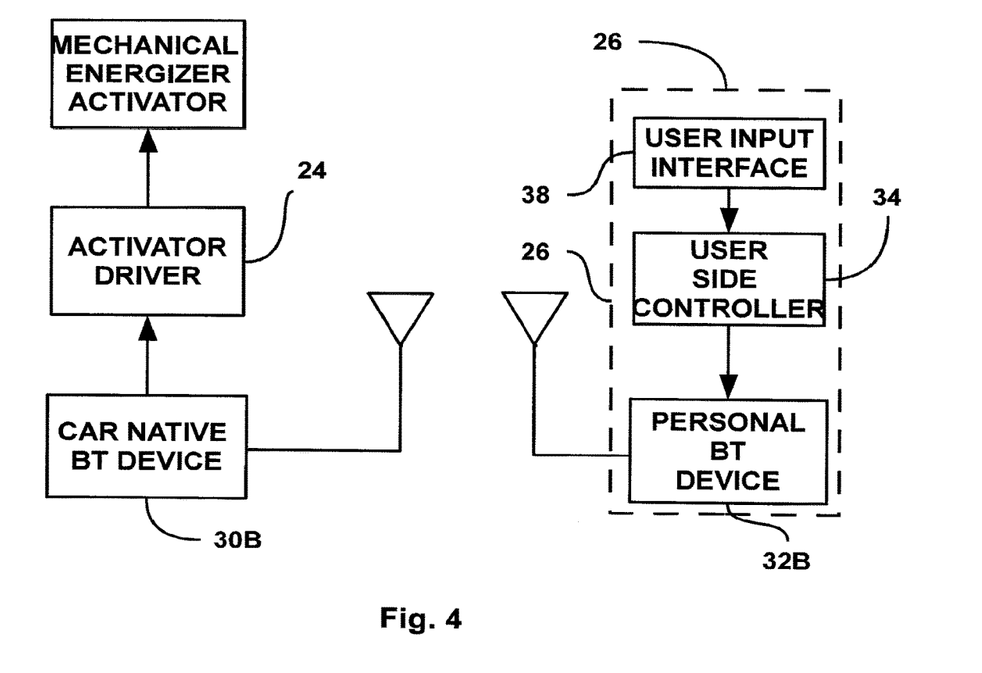
FIG. 4 is a block diagram illustrating a specific embodiment of the system of the invention.
Figures 7, 8:
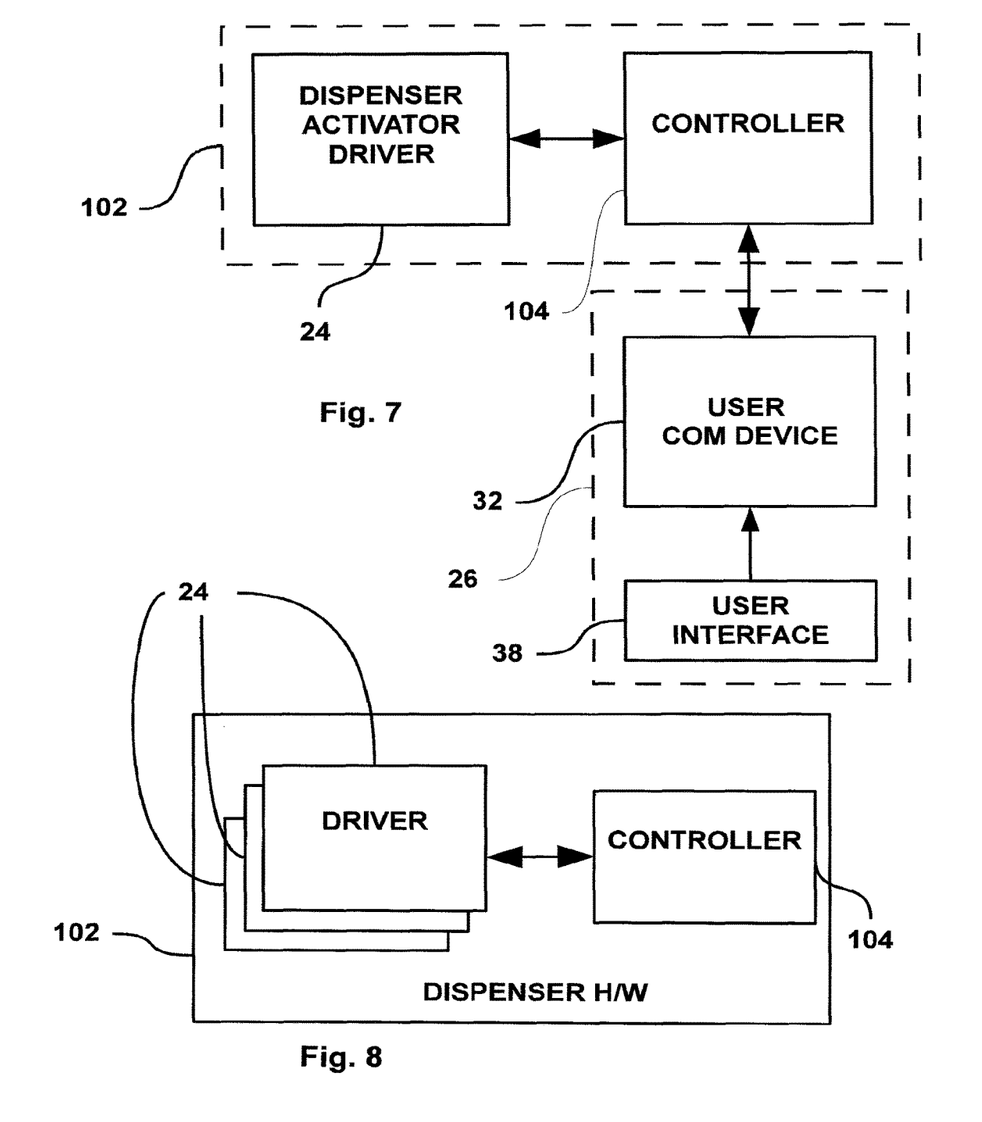
FIG. 7 is a block diagram showing more details of the hardware modules forming the connection between the user channel and the resident hardware.
FIG. 8 is a block diagram showing some details of dispenser part of the resident hardware.

Referring to FIG. 7, which is a detailed version of AN embodiment of the invention and 4, dispenser hardware 102 includes the mechanical parts (such as atomizer activator driver 24, container 72 (not shown), the piezoelectric actuator, and controller 104. The resident communications channel may be a Bluetooth native to the car, or any Bluetooth hardware especially installed for implementing scent dispensation, or any other communication tasks in addition. The two modules, i.e. the communications channel and the scent dispenser are resident statically in the cabin, or in a room or any other space to which scent dispensation is required and are therefore related to as resident hardware 106, or a part of it. User com device 32 connects wirelessly to resident channel. User interface 38 is a term that relates to touch screen, keyboard (physical or virtual), microphone etc.

In FIG. 8 to which reference is now made, dispenser hardware 102 is further detailed. Drivers 24 are the set of actuator drivers that drive each of the actuators of the dispersing systems, respectively. Controller 104 supplies control parameters to the drivers.

Although the term atomizer is often used in the present disclosure to refer to the mode of dispensing activation, it should be pointed out that other techniques exist that do not atomize scent bearing substance for the same purpose, for example as noted above at paragraph 003.

A regards the term resident (followed by hardware or device) the meaning is that the hardware is a part of the vehicle itself, or otherwise attached to the vehicle specifically because it is to form a contact with the dispensing device. Thus a resident device may be attached to the dispensing device, such as may be even packaged together. Another option is that the resident com channel hardware is connected to the activator by wire.

DAS Parameters

The intervention of the user in the contents of the DAS (dispenser activation schemes) relates to choice factors that the user may implement by applying an input element such as a keyboard. In addition, some parameters of the DAS may change as a result of routines kept in the memory of the controller or in the user corn device 32 (see FIG. 3) The user may enter (input) some parameters through an application on his/her smartphone, for example, the choice of scents or combination of scents may be entered by the touch screen of the smartphone, once the relevant application has been invoked. Scent intensity may also be selected and implemented through the use of a keyboard of the smartphone. Once the choice has been made, the parameter is sent to the car com device 34, in the case of a car, and injected then to the controller 26, which selects the appropriate SDU/s, and inputs the parameters for the DAS. For example scent intensity may be interpreted by the DAS as shortening the time passing between each burst of scent ejection. A stored program in the controller may for example invoke a "summer scheme" or a "winter scheme", based on the date provided by the user hardware.

In another option, the resident hardware contains a set of default parameters that when the resident hardware is activated, the default set takes precedence until the DAS instructs otherwise.

Resonance Frequency Verification

Figure 9:
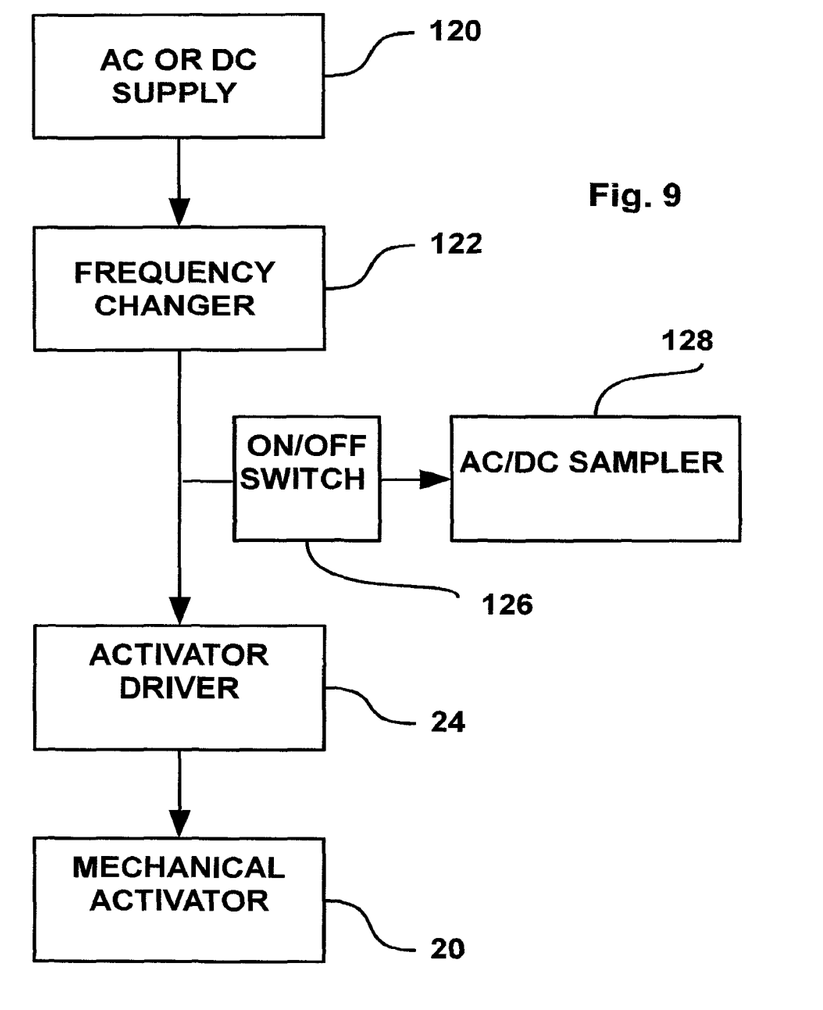
FIG. 9 is a block diagram describing the hardware elements facilitating resonance frequency verification of the piezoelectric actuator in an embodiment of the invention.

As mentioned above resonance frequency check of the scent dispensing unit (SDU) may be carried out on several occasions, such as before starting the scent ejection, or as a part of the DAS. In FIG. 9 a schematic hardware assembly through which resonance frequency verification is facilitated. AC or DC supply 120 is injected to frequency changer 122 which feeds activator driver 24. Piezoelectric activator 20 is fed by driver 24. To determine resonance, on/off switch 126 is turned on and AC/DC sampler 128 is activated. As frequency is changed, the current is measured such as when current reaches its peak, resonance frequency is established.

Automatic Activation and Shut-Off of the Dispensation System

The BT network is an ad hoc network which is formed and disrupted at will or automatically. After "pairing" (introduced above in paragraph 022) is performed once, forming of the network between the two paired BT devices can be made without intentional intervention of the user. Thus, a user who had his/her personal device paired can form a network with the resident system in the car automatically as he/she approaches the resident BT device in the car. When that user leaves the car/premises and a threshold distance between the resident device is surpassed, the network disrupts. The system can be programmed to automatically send (transmit) an application protocol to the resident channel once a network has been formed or activation of the dispenser automatically once a network has been formed and conversely send a "terminate activation" command when the network has been disrupted or deactivation of the dispenser automatically once a network has been disrupted.

Another automation option is applying a time constraint on the duration of activity of the dispenser. For example if the dispenser is turned on automatically as the network initiates, nevertheless it can be stopped once a timer in the user side send a "terminate" command over to the resident side. Cyclical activity may be implemented just the same. Another aspect is that the DAS contains a lag period so that the dispenser is not activated immediately upon sending it over to the resident hardware.

Personalization

Since BT is a master-slave multi user network, the architecture can be arranged such that several users may pair with the same resident BT device, each of the users BT assuming a slave function. The resident BT system, a master, would recognize the specific user connecting and once a network has formed the specific user sends the DAS kept in the memory of his/her device. For example, a certain user shows preference for a certain fragrance, the DAS of his/her choice would include reference to the appropriate container containing the appropriate substance. The AP mentioned above can also be used to cause specific parameters on the SDU to affect the parameters of its cyclic activity.

The invention claimed is:

1. An apparatus for dispensing compounds bearing scent, comprising:

a. at least one scent dispensing unit comprising at least one scent bearing compound and an electromechanical dispenser providing droplets to the ambient atmosphere, b. an user-handled hardware comprising a user-handled hardware controller, a memory, a communications device and a user interface through which input parameters are inputted to a dispenser activation profile;
c. resident hardware for controlling said electromechanical dispenser; said resident hardware comprising a resident hardware controller activating said electromechanical dispenser by using an activator driver according to a predetermined activation profile;
d. a wireless peer to peer channel implementing the communications between said user-handled device and said resident hardware; and wherein said resident hardware controller is preprogrammed to activate said electromechanical dispenser by using said activator driver according to a predetermined activation profile in a vehicle, in a room or cabinet.

2. The apparatus according to claim 1, wherein said user-handled hardware is at least one smartphone or tablet computer paired with said resident hardware.

3. The apparatus according to claim 2, wherein a GPS receiver absolute position and speed of said user-handled hardware are measured and are registered in said user-handled hardware, when said user-handled hardware and resident hardware wireless peer to peer channel is deactivated since wireless connection between said user-handled hardware and resident hardware is interrupted.

4. The apparatus according to claim 1, wherein said activation profile comprises at least one parameter of a duty cycle selected from the group consisting of frequency of vibration bursts, number of said vibration bursts per unit time, duration of said bursts and any combination thereof.

5. The apparatus according to claim 4, wherein said activation profile where the unit active time—the on time combination duration of said vibration bursts are accumulated, registered or saved in the resident hardware memory.

6. The apparatus according to claim 5, wherein said unit active time—the on time combination duration of said vibration bursts that were accumulated, registered or saved in the resident hardware memory are sent via the said interconnected peer to peer wireless link to the said user-handled hardware.

7. The apparatus as in claim 5, wherein said wireless peer to peer channel is a Bluetooth channel a Classic or Bluetooth Low Energy channel.

8. A method for controlling the dispensation of scent into the ambient atmosphere by a scent dispending unit, said method comprising the steps of:
a. providing an apparatus for dispensing compounds bearing scent comprising:
  i. at least one scent dispensing unit comprising at least one scent bearing compound and an electromechanical dispenser providing droplets to the ambient atmosphere,
  ii. an user-handled hardware comprising a controller, a memory a communications device and a user device interface through which input user parameters are inputted to an activation profile of said dispenser;
  iii. resident hardware for controlling said at least one scent dispenser; said resident hardware comprising a controller activating said electromechanical dispenser by using an activator driver; and
  iv. a wireless peer to peer channel implementing the communications between said user-handled device and said resident hardware;
b. forming a wireless peer to peer channel by interconnecting said user-handled hardware and resident hardware;
c. transmitting activation profile from said user hardware;
d. transmitting at least one dispenser activation profile which includes frequency of vibration parameter and an activation duty cycle to said resident hardware;

wherein said resident hardware controller is preprogrammed to activate said electromechanical dispenser by using said activator driver according to a predetermined activation profile in a vehicle or in a room or cabinet.

9. The method according to claim 8, wherein said user-handled hardware and resident hardware are interconnected by said wireless peer to peer channel and deactivated when wireless connection between said user handled hardware and resident hardware is interrupted.

10. The method according to claim 9, wherein said GPS receiver absolute position and speed of said user-handled hardware are measured and are registered in said user-handled hardware, when said user-handled hardware and resident hardware wireless peer to peer channel is deactivated since wireless connection between said user-handled hardware and resident hardware is interrupted.

11. The method according to claim 9, wherein said activation profile where the unit active time—the on time combination duration of said vibration bursts are accumulated, registered or saved in the resident hardware memory.

12. The method according to claim 8, wherein said user-handled hardware and resident hardware are interconnected by said wireless peer to peer channel and deactivated when wireless connection between said user handled hardware and resident hardware is interrupted.

13. The method according to claim 12 wherein said GPS receiver absolute position and speed of said user-handled hardware are measured and are registered in said user-handled hardware, when said user-handled hardware and resident hardware wireless peer to peer channel is deactivated since wireless connection between said user-handled hardware and resident hardware is interrupted.

14. The method according to claim 12, wherein said unit active time—the on time combination duration of said vibration bursts that were accumulated, registered or saved in the resident hardware memory are sent via the said interconnected peer to peer wireless link to the said user-handled hardware.

* * * * *